(12) United States Patent
Lou et al.

(10) Patent No.: US 8,389,926 B2
(45) Date of Patent: Mar. 5, 2013

(54) TESTING APPARATUS FOR LIGHT-EMITTING DEVICES WITH A DESIGN FOR A REMOVABLE SENSING MODULE

(75) Inventors: Choon Leong Lou, Hsinchu (TW); Li Min Wang, Hsinchu (TW); Yi Ming Lau, Hsinchu (TW); Ho Yeh Chen, Hsinchu (TW)

(73) Assignee: Star Technologies Inc., Hsinchu (TW)

( * ) Notice: Subject to any disclaimer, the term of this patent is extended or adjusted under 35 U.S.C. 154(b) by 346 days.

(21) Appl. No.: 12/857,310

(22) Filed: Aug. 16, 2010

(65) Prior Publication Data

US 2011/0062317 A1 Mar. 17, 2011

Related U.S. Application Data

(60) Provisional application No. 61/242,131, filed on Sep. 14, 2009.

(51) Int. Cl.
*H01J 5/02* (2006.01)

(52) U.S. Cl. .................................. 250/239; 250/214.1
(58) Field of Classification Search .................. 250/239, 250/214.1, 216; 257/80–84, 432–435; 219/388–405, 247
See application file for complete search history.

(56) References Cited

U.S. PATENT DOCUMENTS

| 4,594,613 | A | * | 6/1986 | Shinbori et al. | 348/340 |
| 4,896,217 | A | * | 1/1990 | Miyazawa et al. | 348/340 |
| 6,389,687 | B1 | * | 5/2002 | Glenn et al. | 29/832 |
| 2008/0297771 | A1 | | 12/2008 | Ou et al. | |

* cited by examiner

*Primary Examiner* — Que T Le
(74) *Attorney, Agent, or Firm* — WPAT, P.C.; Anthony King

(57) ABSTRACT

A sensing module for light-emitting devices includes a circuit board having at least one retaining region configured to retain an optical sensor, at least one circuit configured to electrically connect the optical sensor to an output interface at a front end of the circuit board, a substrate positioned on the circuit board and having at least one aperture exposing the retaining regions, and an optical device positioned on the aperture and configured to collect emitting lights from a light-emitting device to the retaining region through the aperture.

12 Claims, 7 Drawing Sheets

TESTING APPARATUS FOR LIGHT-EMITTING DEVICES WITH A DESIGN FOR A REMOVABLE SENSING MODULE

BACKGROUND OF THE INVENTION

1. Technical Field

The present invention relates to a testing apparatus for light-emitting devices, and more particularly, to a testing apparatus with a design for a removable sensing module configured to load at least one optical sensor into the testing oven in a removable manner without affecting the high temperature environment within the testing apparatus.

2. Background

Light emitting diodes (LED) are well known in the art. Testing of LEDs involves measurement of the light intensity emitted by the LED devices at a predefined wavelength spectrum. To ensure accurate comparative testing of the LED devices, the light emitted by the devices must be collected at a precise, reproducible manner, e.g., at a predefined distance or angle, and delivered to a light detector using appropriate optics.

Due to the high volume of required reliability data which is usually collected over a long time, these devices are diced and packaged into individual packages and tested over high temperature condition in a testing apparatus. The next level of quality assurance is to ensure that all infant failures are eliminated through a burn-in test before shipping to customers. The LEDs formed on the wafer are cut so as to separate the dies. Each die is then assembled into a light-emitting package with bond wires connecting the bond pads of the die with the pins of the package. Once the die is assembled in a package it undergoes a burn-in test to ensure the quality and reliability of the light-emitting devices. It is absolutely necessary to conduct the burn-in test, which is a screening test held under high temperatures in a testing apparatus in order to eliminate early failures before shipment.

US 2008/0297771 discloses a high-speed optical sensing device including an optical detector, a lens set, and a splitter. The optical detector is utilized for detecting luminous intensity, the lens set is utilized for concentrating light beams toward a color analyzer, and the splitter is aligned to the illuminating device to be tested and is utilized to separate the light beam generated by the illuminating device to the optical detector and the lens set simultaneously.

SUMMARY

One aspect of the present invention provides a testing apparatus with a design for a removable sensing module configured to load at least one optical sensor into the testing oven in a removable manner without affecting the high temperature environment within the testing apparatus.

A sensing module for light-emitting devices according to this aspect of the present invention comprises a circuit board including at least one retaining region configured to retain an optical sensor, at least one circuit configured to electrically connect the optical sensor to an output interface at a front end of the circuit board; a substrate positioned on the circuit board and having at least one aperture exposing the retaining regions; and an optical device positioned on the aperture and configured to collect emitting lights from a light-emitting device to the retaining region through the aperture.

A testing apparatus for light-emitting devices according to another aspect of the present invention comprises an oven including a front wall having at least one front opening; a carrier module configured to load at least one light-emitting device into the oven through the front opening in a removable manner; and a sensing module configured to load at least one optical sensor into the oven through the front opening in a removable manner. In one embodiment of the present invention, the sensing module comprises a circuit board including at least one retaining region configured to retain the optical sensor, at least one circuit configured to electrically connect the optical sensor to an output interface at a front end of the circuit board; a substrate positioned on the circuit board and having at least one aperture exposing the retaining regions; and an optical device positioned on the aperture and configured to collect emitting lights from a light-emitting device to the retaining region through the aperture.

Due to the design for the sensing module which allows for removal through the front opening of the front wall, the testing apparatus of the present invention allows the operator to load the optical sensor into the testing oven without affecting the high temperature environment within the testing apparatus. In addition, the removable design of the sensing module allows operators not to continuously place the expensive optical sensors in the testing environment at high temperature and/or high humidity so as to prevents the optical sensors from being degraded under the high temperature and/or high humidity in the oven over long stress time. This helps prevent damage to the optical sensor, and the damage of the optical sensor obviously affects the accuracy of the optical test data.

The foregoing has outlined rather broadly the features and technical advantages of the present invention in order that the detailed description of the invention that follows may be better understood. Additional features and advantages of the invention will be described hereinafter, and form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

The objectives and advantages of the present invention are illustrated with the following description and upon reference to the accompanying drawings in which.

DETAILED DESCRIPTION

Figure 1:
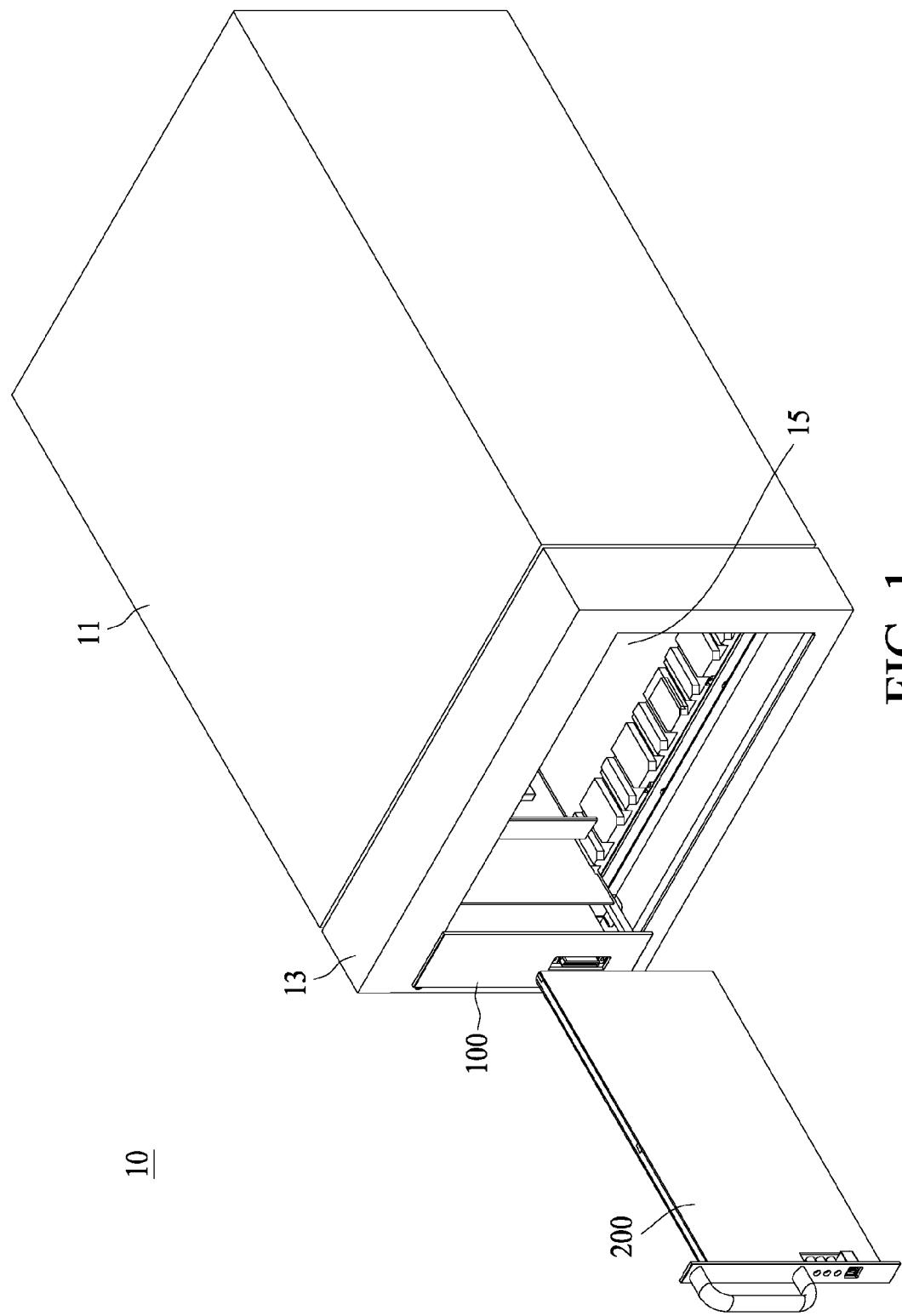
FIG. 1 and FIG. 2 illustrate a testing apparatus for light-emitting devices according to one embodiment of the present invention.
Figure 2:
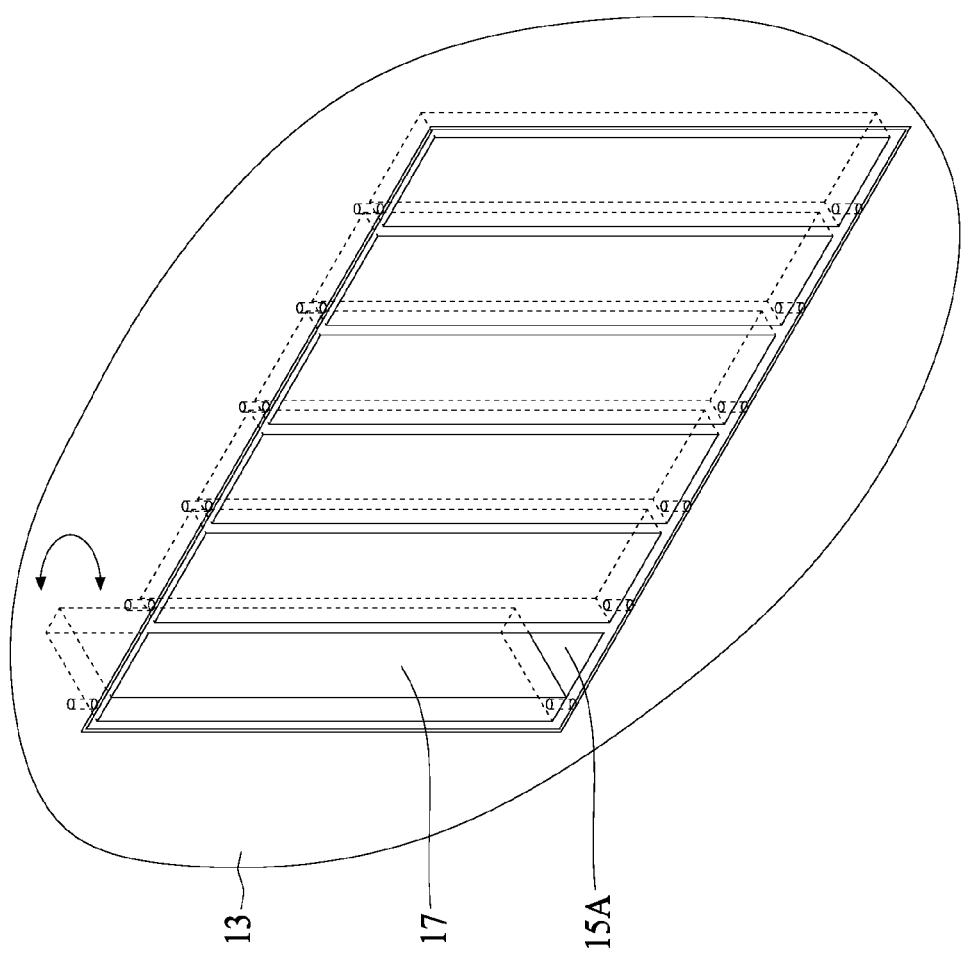

FIG. 1 and FIG. 2 illustrate a testing apparatus 10 for light-emitting devices 123 according to one embodiment of the present invention. Referring to FIG. 1, the testing apparatus 10 comprises an oven 11 including a front wall 13 having at least one front opening 15, a carrier module 100 configured to load light-emitting devices 123 (shown in FIG. 3) into the oven 11 through the front opening 15 in a removable manner, and a sensing module 200 configured to load at least one optical sensor such as the optical sensor 213 (shown in FIG. 6) into the oven 11 through the front opening 15 in a removable manner. In one embodiment of the present disclosure, the optical sensor 213 can be the photo detector or the spectrum analyzer.

Referring to FIG. 2, in one embodiment of the present invention, the front wall 13 has a plurality of front openings 15A each with a self-closing door 17 to isolate the internal testing environment of the testing apparatus 10 from the surrounding environment. Consequently, the testing apparatus 10 allows the carrier module 100 and the sensing module 200 to be inserted into and removed from the oven 11 through the front openings 15A of the front wall 13; in other words, the testing apparatus 10 of the present invention allows the operator to load the optical sensor 213 and the light-emitting device 123 into the testing oven 11 without affecting the high temperature environment within the testing apparatus 10.

Figure 3:
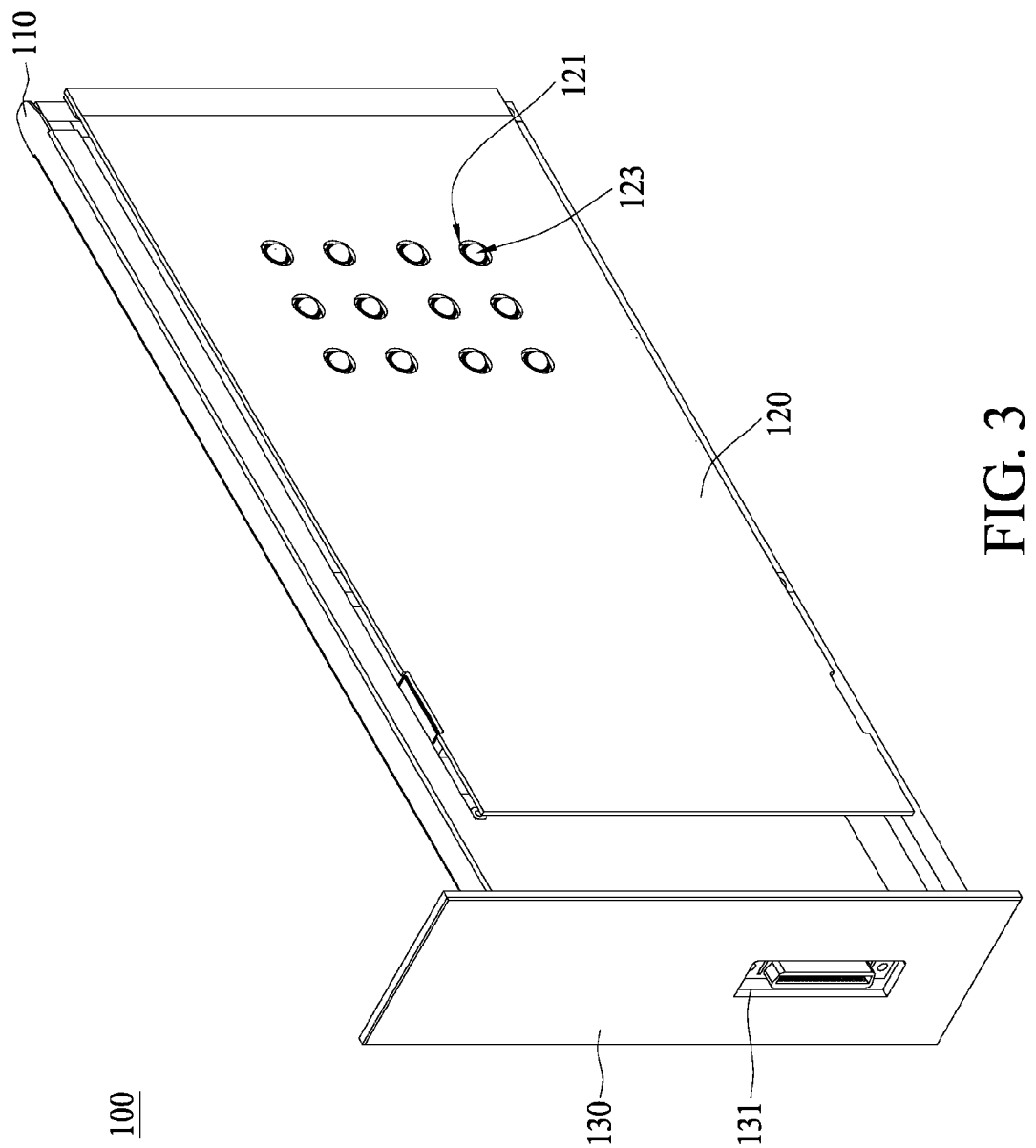
FIG. 3 illustrates a carrier module according to one embodiment of the present invention.

FIG. 3 illustrates a carrier module 100 according to one embodiment of the present invention. In one embodiment of the present invention, the carrier module 100 includes a frame 110, a circuit board 120 positioned on one side of the frame 110 and having a plurality of holes 121 with the light-emitting devices 123 under test positioned inside the holes 121, and a front plate 130 with an electrical connector 131. In one embodiment of the present disclosure, the electrical connector 131 is electrically connected to a tester (not shown in the drawings), which controls the testing process, including setting parameters such as the applied current to the light-emitting devices 123 during the testing process.

Figure 4:
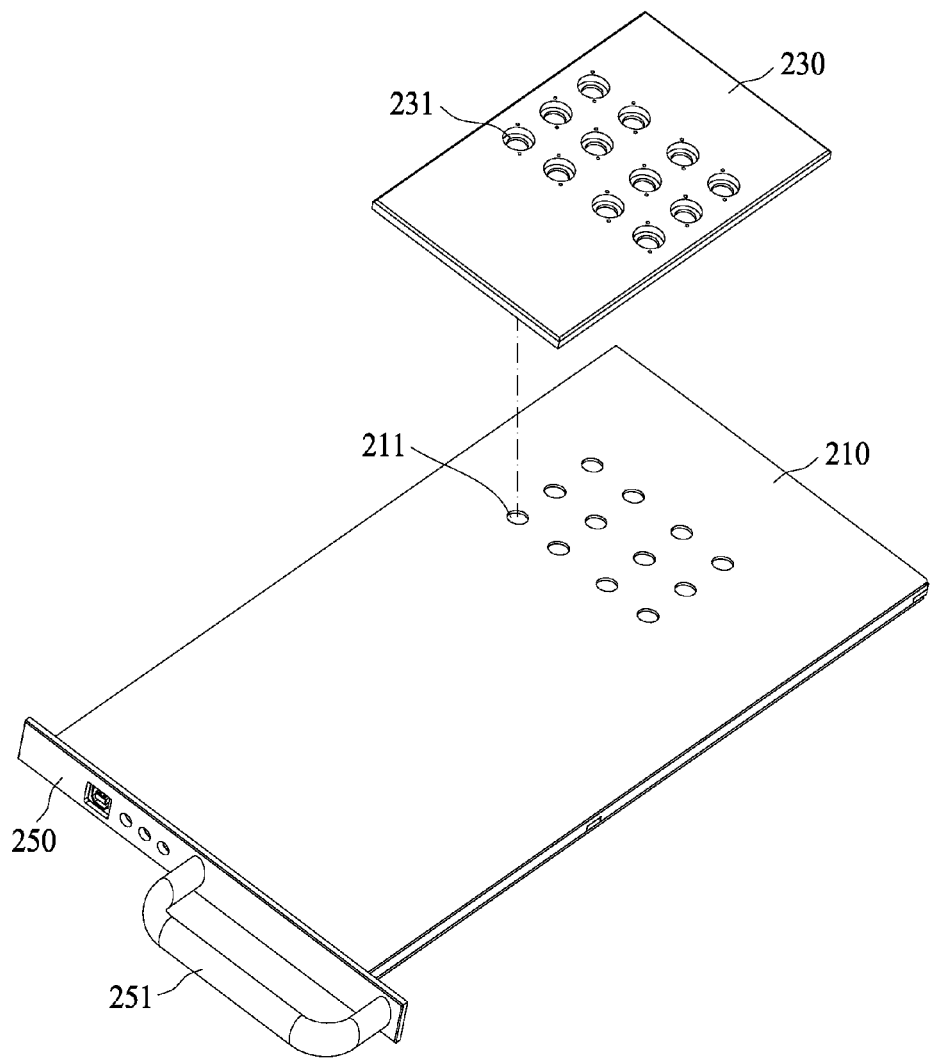
FIG. 4 to FIG. 6 illustrate a sensing module according to one embodiment of the present invention.
Figure 5:
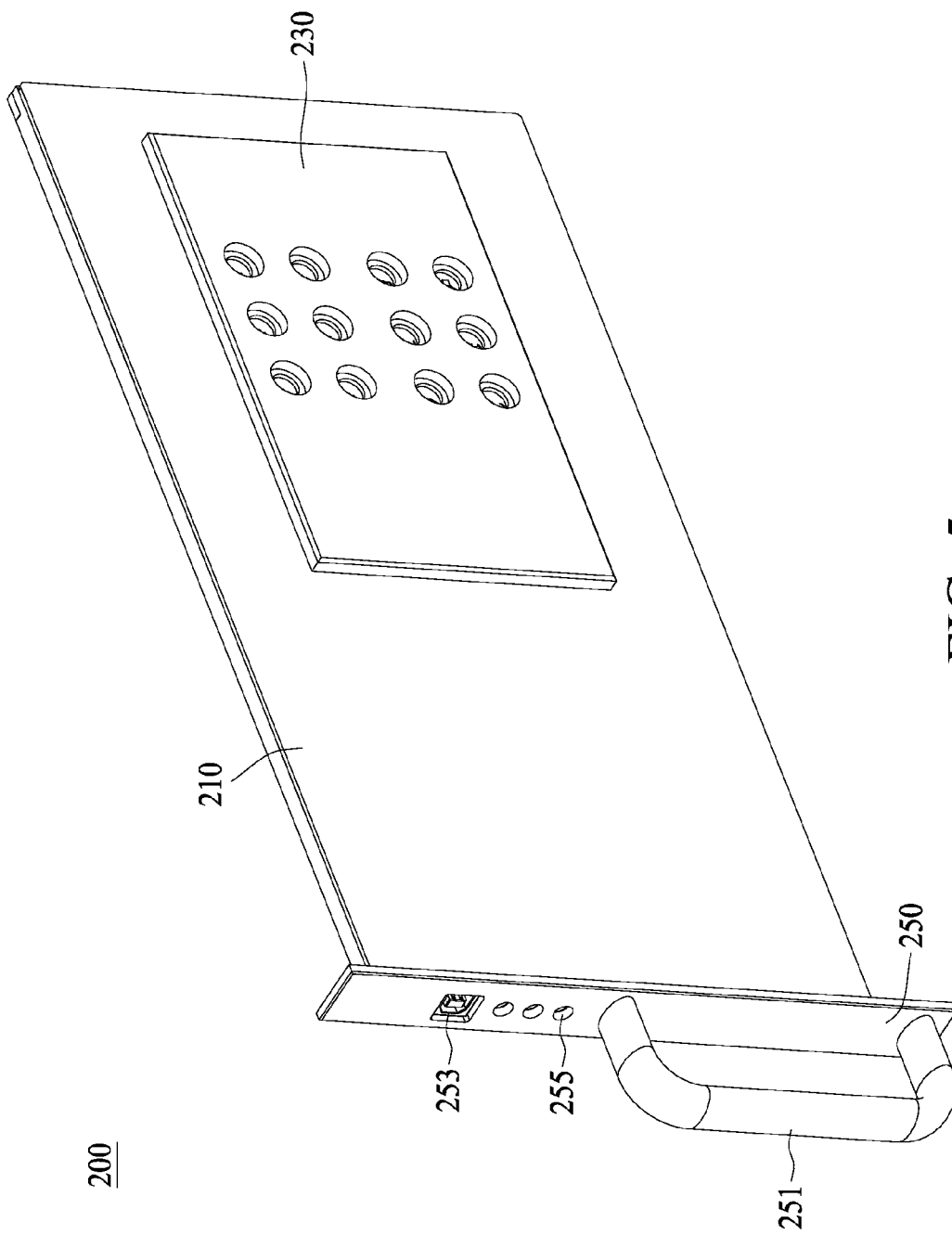
Figure 6:
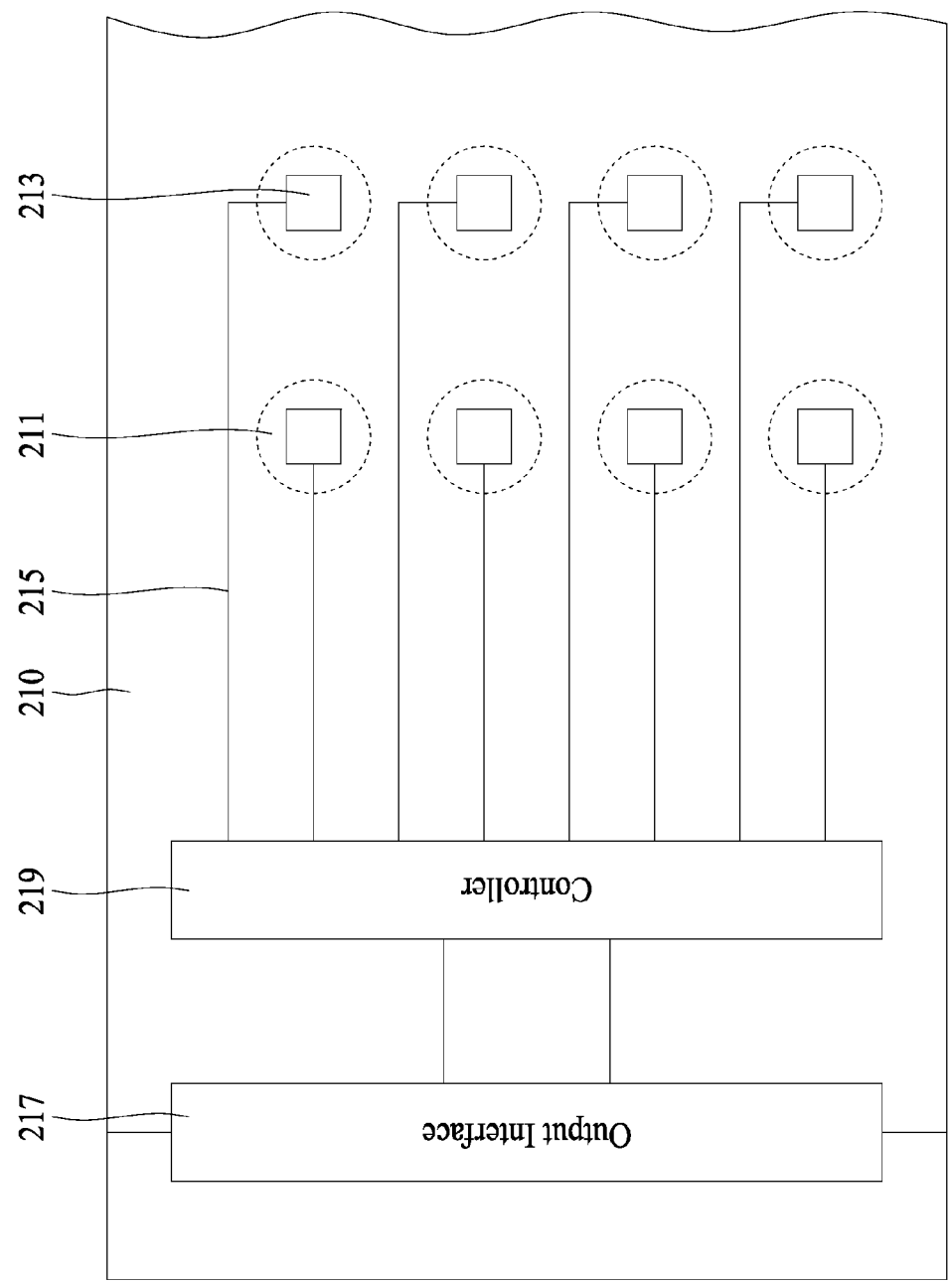

FIG. 4 to FIG. 6 illustrate a sensing module 200 according to one embodiment of the present invention. In one embodiment of the present invention, the sensing module 200 comprises a circuit board 210 including at least one retaining region 211 configured to retain the optical sensor 213, at least one circuit 215 configured to electrically connect the optical sensor 213 to an output interface 217 at a front end of the circuit board 210, and a substrate 230 positioned on the circuit board 210 and having at least one aperture 231 exposing the retaining regions 211. In one embodiment of the present invention, the sensing module 200 further comprises a controller 219 positioned on the circuit board 210 and electrically connected to the optical sensors 213, and the controller 219 is configured to control the operation of the optical sensors 213. In one embodiment of the present invention, the retaining regions 211 are configured to retain a plurality of optical sensors 211 arranged in an array manner.

In one embodiment of the present invention, the sensing module 200 further comprises a front plate 250 positioned at the front end of the circuit board 210 and a grip member 251 positioned at the front end of the circuit board 250, i.e., on the front plate 250. In one embodiment of the present invention, the front plate 250 includes an electrical connector 253 electrically connected to the circuit 215 via the output interface 217 on the circuit board 210. In one embodiment of the present invention, the front plate 250 further includes at least one indicator 255 electrically connected to the circuit 215, and the indicator 255 is configured to display the operation state of the optical sensor 213.

During the testing process of the light-emitting device 123 under test, the sensing module 200 is inserted into the oven 11 through the front opening 15 such that the light-emitting device 123 on the carrier module 100 faces a respective optical sensor 213 on the sensing module 200, and the electrical connector 253 is electrically connected to a tester (not shown in the drawings), which accumulates the sensing data of the optical sensor 213 for further analysis to determine whether the light-emitting device 123 under test complies with the predetermined specification. Once the sensing is completed, the sensing module 200 is preferably removed from the front opening 15 to the outside of the oven 11, rather than remaining in the testing environment while the sensing is not performed.

Figure 7:
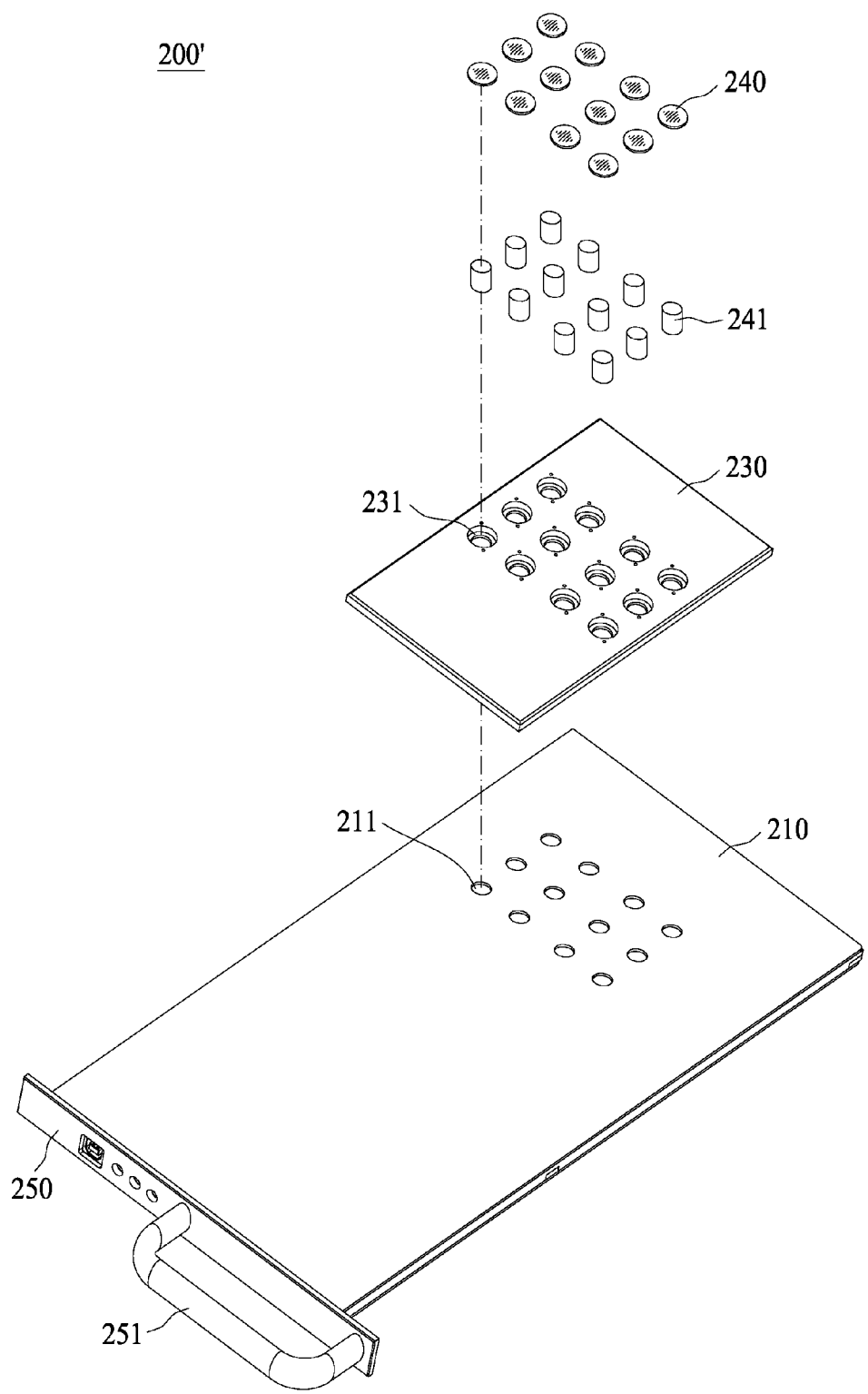
FIG. 7 illustrates a sensing module according to one embodiment of the present invention.

FIG. 7 illustrates a sensing module 200' according to one embodiment of the present invention. In one embodiment of the present invention, in contrast to the sensing module 200 shown in FIG. 4, the sensing module 200' further comprises an optical device 240 such as optical lenses (for example, a condenser) positioned on the aperture 231 and configured to collect emitting lights from the light-emitting device 123 to the optical sensor 213 in the retaining region 211 through the aperture 231. In one embodiment of the present invention, the sensing module 200' further includes an optical tube 241 such as a light integrator between the optical device 240 and the retaining region 211. Preferably, the optical tube 241 has a first end substantially in focus of the optical lenses 240 and a second end on the retaining region 211.

The optical sensors, i.e., photo detectors or spectrum analyzer, are relatively more expensive than the light-emitting devices under test, and the optical testing of the light-emitting devices does not require continuous monitoring of the emitting power of the light-emitting devices during the testing process. Therefore, it is not necessary to place the expensive optical sensors in the testing environment at high temperature and/or high humidity; instead, the optical sensors are not exposed to the testing environment for a long term as the light-emitting device under test to avoid damage to the optical sensor.

In particular, the removable design of the sensing module allows operators not to continuously place the expensive optical sensors in the testing environment at high temperature and/or high humidity so as to prevents the optical sensors from being degraded under the high temperature and/or high humidity in the oven over long stress time. This helps prevent damage to the optical sensor, and the damage of the optical sensor obviously affects the accuracy of the optical test data. In addition, due to the removable design for the sensing module which allows for removal through the front opening of the front wall, the testing apparatus of the present disclosure allows the operator to load the optical sensor temporarily into the testing oven without affecting the high temperature environment within the testing apparatus.

Although the present invention and its advantages have been described in detail, it should be understood that various changes, substitutions and alterations can be made herein without departing from the spirit and scope of the invention as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A testing apparatus for light-emitting devices, comprises:

an oven including a front wall having at least one front opening;

a carrier module configured to load at least one light-emitting device into the oven through the front opening in a removable manner; and a sensing module configured to load at least one optical sensor into the oven through the front opening in a removable manner, the sensing module including:

a circuit board including at least one retaining region configured to retain the optical sensor, wherein at least one circuit is configured to electrically connect the optical sensor to an output interface at a front end of the circuit board;

a substrate positioned on the circuit board and having at least one aperture exposing the retaining regions; and an optical device positioned on the aperture and configured to collect emitting lights from a light-emitting device to the retaining region through the aperture.

2. The testing apparatus for light-emitting devices of claim 1, wherein the circuit board includes a plurality of retaining regions configured to retain a plurality of optical sensors and a plurality of circuits configured to electrically connect the optical sensors to the output interface.

3. The testing apparatus for light-emitting devices of claim 2, wherein the sensing module further comprises a controller positioned on the circuit board and electrically connected to the optical sensors, wherein the controller is configured to control the operation of the optical sensors.

4. The testing apparatus for light-emitting devices of claim 3, wherein the retaining regions are configured to retain a plurality of optical sensors arranged in an array manner.

5. The testing apparatus for light-emitting devices of claim 1, wherein the sensing module further comprises a grip member positioned at the front end of the circuit board.

6. The testing apparatus for light-emitting devices of claim 1, wherein the sensing module further comprises a front plate positioned at the front end of the circuit board.

7. The testing apparatus for light-emitting devices of claim 6, wherein the front plate includes an electrical socket electrically connected to the circuit.

8. The testing apparatus for light-emitting devices of claim 6, wherein the front plate includes at least one indicator electrically connected to the circuit, and the indicator is configured to display the operation state of the optical sensor.

9. The testing apparatus for light-emitting devices of claim 1, wherein the optical device includes an optical lens.

10. The testing apparatus for light-emitting devices of claim 9, wherein the optical device further includes an optical tube with a first end substantially in focus of the optical lenses and a second end on the retaining region.

11. The testing apparatus for light-emitting devices of claim 1, wherein the oven includes a self-closing door for the front opening.

12. The testing apparatus for light-emitting devices of claim 1, wherein the oven includes a plurality of front openings.

* * * * *